US 6,740,071 B2

(12) United States Patent
Gibbs

(10) Patent No.: US 6,740,071 B2
(45) Date of Patent: May 25, 2004

(54) ABSORBENT GARMENT TAB HAVING ZONES OF DIFFERENT ELASTICITY

(75) Inventor: Bernadette M. Gibbs, Statham, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 64 days.

(21) Appl. No.: 10/012,410

(22) Filed: Dec. 12, 2001

(65) Prior Publication Data

US 2003/0109843 A1 Jun. 12, 2003

(51) Int. Cl.[7] .................... A61F 13/15; A61F 13/20
(52) U.S. Cl. .................. 604/392; 604/389; 604/391
(58) Field of Search ............... 604/385.03, 385.04, 604/385.24, 385.3, 385.31, 386, 389, 392

(56) References Cited

U.S. PATENT DOCUMENTS

| | | | |
|---|---|---|---|
| 3,800,796 A | 4/1974 | Jacob | |
| 4,610,678 A | 9/1986 | Weisman et al. | |
| 4,645,501 A | 2/1987 | Teed | |
| 4,646,362 A | 3/1987 | Heran et al. | |
| 4,787,897 A | 11/1988 | Torimae et al. | |
| 5,098,423 A | 3/1992 | Pieniak et al. | |
| 5,137,537 A | 8/1992 | Herron et al. | |
| 5,147,345 A | 9/1992 | Young et al. | |
| 5,281,207 A | 1/1994 | Chmielewski et al. | |
| 5,464,401 A | 11/1995 | Hasse et al. | |
| 5,496,298 A | 3/1996 | Kuepper et al. | |
| H1565 H | 7/1996 | Brodof et al. | |
| 5,593,401 A | 1/1997 | Sosalla et al. | |
| 5,605,735 A | * 2/1997 | Zehner et al. | 428/100 |
| 5,624,429 A | * 4/1997 | Long et al. | 604/391 |
| 5,695,488 A | 12/1997 | Sosalla | |
| 5,807,368 A | 9/1998 | Helmer | |
| 5,879,341 A | 3/1999 | Odorzynski et al. | |
| 6,068,620 A | 5/2000 | Chmielewski | |
| 6,132,411 A | 10/2000 | Huber et al. | |
| 6,221,483 B1 | * 4/2001 | Hilston et al. | 428/343 |
| 6,255,236 B1 | * 7/2001 | Cree et al. | 442/328 |
| 6,313,372 B1 | 11/2001 | Suzuki | |
| 6,461,715 B1 | * 10/2002 | Guenther et al. | 428/131 |
| 2003/0055394 A1 | * 3/2003 | Gibbs | |

FOREIGN PATENT DOCUMENTS

| | | |
|---|---|---|
| JP | 40-11543 | 6/1940 |
| WO | WO 9516425 A1 * | 6/1995 |

* cited by examiner

*Primary Examiner*—Karin Reichle
(74) *Attorney, Agent, or Firm*—Hunton & Williams

(57) ABSTRACT

A fastener tab for securing absorbent garments having a first elastic region that extends laterally outward from a waist region of the garment, a second elastic region that extends laterally outward from the first elastic region, and a grip that is attached to an outboard portion of the second elastic region. The first elastic region has a greater stretch resistance than the second elastic region. The fastener tab may have a substantially inelastic region interposed between the first elastic region and the second elastic region.

52 Claims, 6 Drawing Sheets

Fig. 9 - Prior Art
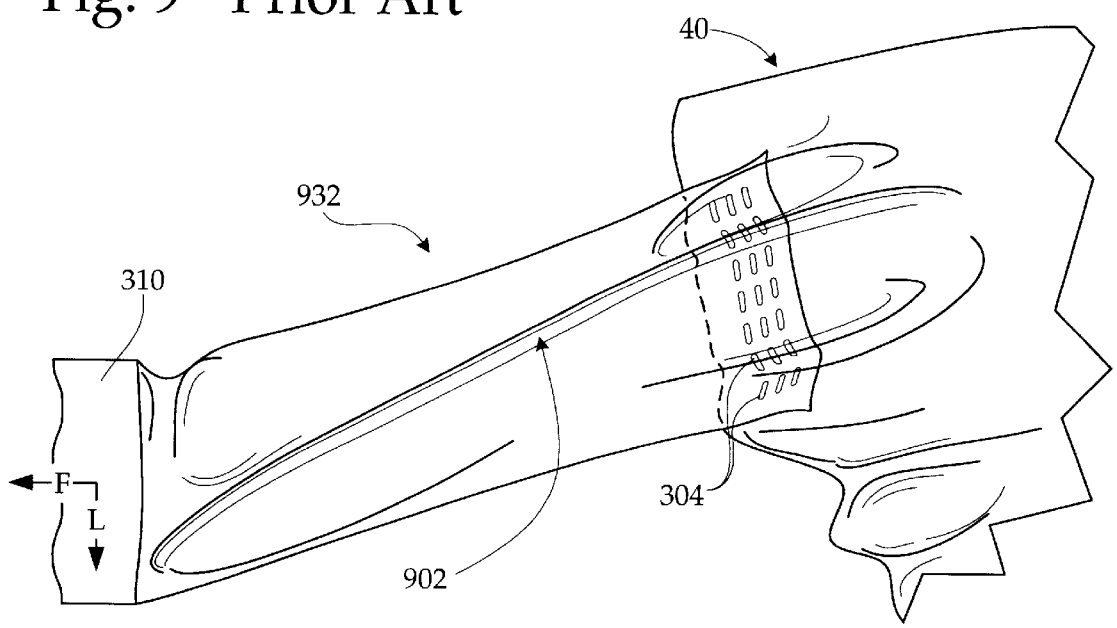
Fig. 10
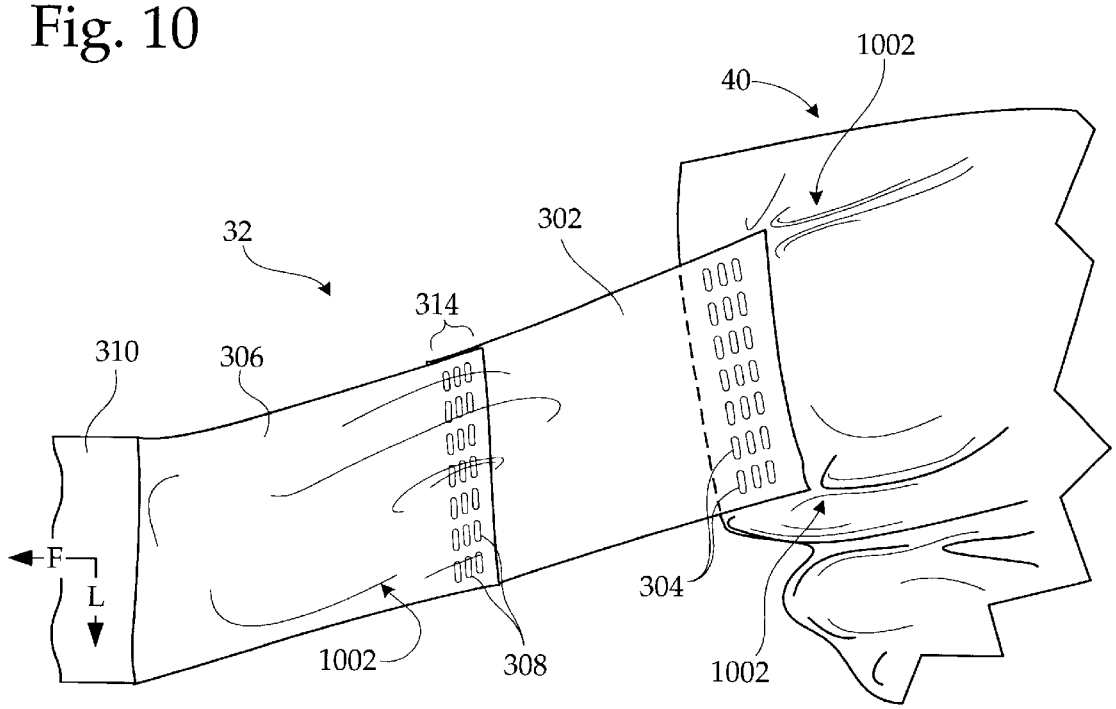

ABSORBENT GARMENT TAB HAVING ZONES OF DIFFERENT ELASTICITY

FIELD OF THE INVENTION

The present invention relates generally to fastening devices for absorbent garments. More specifically, the present invention relates to a fastening device for an absorbent garment having multiple elasticized regions, each being located serially outboard of the previous region.

BACKGROUND OF THE INVENTION

Traditionally, disposable absorbent garments such as infant diapers or training pants, adult incontinence products and other such products were constructed with a moisture-impervious outer backsheet, a moisture-pervious body-contacting inner topsheet, and a moisture-absorbent core sandwiched between the liner and backsheet. In typical diaper-type garments, the garment is affixed to a wearer by attaching one or more fastener tabs that extend across the wearer's hips to hold the back and front halves of the garment to one another.

Much effort has been expended to find a desirable design for absorbent garment fastener tabs. The task of designing a universally suitable fastener tab is complicated by the fact that the fasteners are used on a great number of different wearers, all having slightly to very different body shapes and sizes. Also complicating the design of fastener tabs is the fact that the wearers typically move their bodies while the fasteners are attached, sometimes causing the tabs to become loose, uncomfortable or even unfastened. Yet another factor complicating the task of fastener tab design is the fact that the caregivers applying the tabs do so in a variety of ways that may or may not be suitable to properly affix tabs of the particular design being applied.

A number of different tab designs have been explored to provide suitable fit, comfort, leakage prevention, and other benefits. Typical fastener tabs are inelastic plastic tabs having an adhesive or hook-and-loop gripping portion. Such tabs may be attached directly to the diaper chassis or may have an elastic region interposed between the chassis and the inboard edge of the grip, such as is disclosed, for example, in U.S. Pat. No. 5,624,429 issued to Long et al., which is incorporated herein by reference in its entirety and in a manner consistent with the present invention. Other fastener tabs have been made that have an elasticized portion that extends all the way to the end of the tab, and have the grip attached directly to one side of the elastic portion at the outboard end, typically rendering that portion of the fastener tab inelastic. Such tabs are disclosed, for example, in U.S. Pat. No. 3,800,796 issued to Jacob, which is incorporated herein by reference in its entirety and in a manner consistent with the present invention. Still other fastener tabs have been provided with elasticized regions that have intermediate zones, located between the grip and the diaper chassis, having little or no elastic stretchability, such as those disclosed, for example, in U.S. Pat. No. 6,132,411 issued to Huber et al., which is incorporated herein by reference in its entirety and in a manner consistent with the present invention.

Despite these and other efforts by absorbent garment manufacturers and others to provide suitable fastener tabs for absorbent garments, there is still a need to provide a more comfortable, better fitting, and more aesthetically pleasing fastener tab. These are just a few of the disadvantages of the prior art that the preferred embodiments seek to address.

SUMMARY OF THE INVENTION

It would also be desirable to provide fastener tabs that have selectively elasticized regions that provide increased comfort, fit and appearance on moving wearers having a variety of body shapes and sizes.

In accordance with these and other features of various embodiments of the invention, there is provided a fastener tab for securing absorbent garments onto a wearer. The fastener tab has a first elastic region that extends laterally outward from a waist region of the garment, a second elastic region that extends laterally outward from the first elastic region, and a grip that is attached to a laterally outboard portion of the second elastic region. The first elastic region has a greater stretch resistance than the second elastic region.

According to one feature of the invention, the fastener tab may additionally have a substantially inelastic region interposed between the first elastic region and the second elastic region. According to another feature of the invention, the fastener tab's first and second elastic regions may be made from elastic laminates having a central elastic layer located between inelastic layers. According to still another feature of the invention, the grip is a hook portion of a hook-and-loop fastener. According to yet another feature of the invention, the side edges of the fastener tab may be non-parallel.

According to other features of the invention, when a lateral tensile force is applied to the grip to extend the first elastic region to about 110% to about 180% of its original length, the second elastic region is extended to about 160% to about 230% of its original length. In another feature, when a lateral tensile force is applied to the grip to extend the first elastic region to about 130% to about 160% of its original length, the second elastic region is extended to about 175% to about 215% of its original length. And in another feature, when a lateral tensile force is applied to the grip to extend the first elastic region to about 145% of its original length, the second elastic region is extended to about 195% of its original length.

These and other features of the invention will be readily apparent from the Detailed Description that follows, along with reference to the drawings appended hereto.

BRIEF DESCRIPTION OF THE DRAWINGS

FIG. 9 is a plan view of a conventional prior art fastener tab under a lateral tensile force and a vertical load;

FIG. 10 is a plan view of a fastener tab, according to one embodiment of the invention, under a lateral tensile force and a vertical load;

DETAILED DESCRIPTION OF THE PREFERRED EMBODIMENTS

Figure 1:
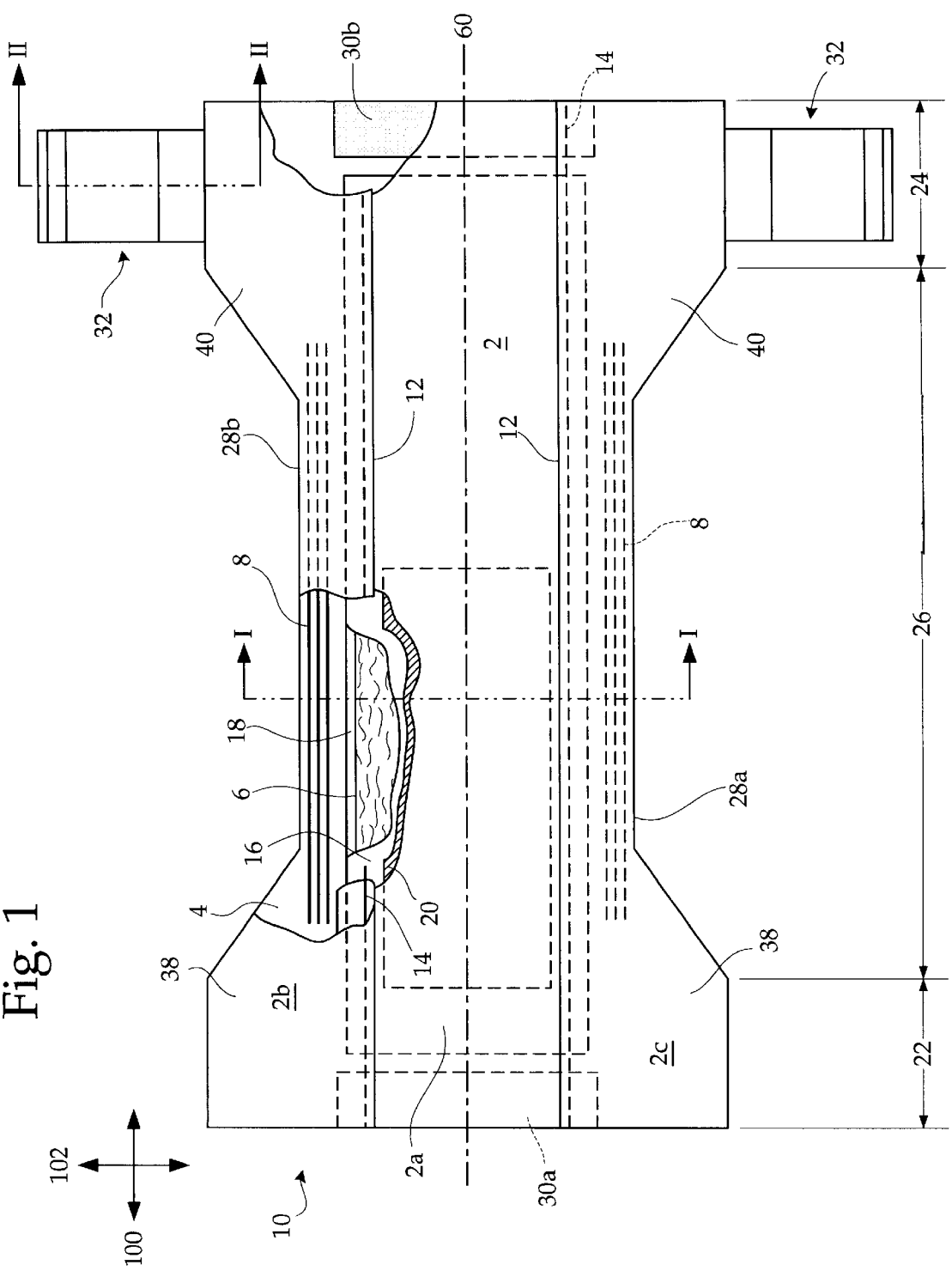
FIG. 1 is a plan view of a diaper-type absorbent garment, shown with the effects of elastics removed for clarity.

As used herein, the term "absorbent garment" or "garment" refers to garments that absorb and contain exudates, and more specifically, refers to garments that are placed against or in proximity to the body of the wearer to absorb and contain the various exudates discharged from the body. A non-exhaustive list of examples of absorbent garments includes diapers, diaper covers, disposable diapers, training pants, feminine hygiene products and adult incontinence products. The term garment includes all variations of absorbent garments, including disposable absorbent garments that are intended to be discarded or partially discarded after a single use (i.e., they are not intended to be laundered or otherwise restored or reused) and unitary disposable absorbent garments that have essentially a single structure (i.e., do not require separate manipulative parts such as a diaper cover and insert). As used herein, the term "diaper" refers to an absorbent garment generally worn by infants and incontinent persons about the lower torso.

The claims are intended to cover all of the foregoing classes of absorbent garments, without limitation, whether disposable, unitary or otherwise. These classifications are used interchangeably throughout the specification, but are not intended to limit the claimed invention. The invention will be understood to encompass, without limitation, all classes of absorbent garments, including those described above.

Absorbent garments and diapers may have a number of different constructions. In each of these constructions it is generally the case that an absorbent core is disposed between a liquid pervious, body-facing topsheet, and a liquid impervious, exterior facing backsheet. In some cases, one or both of the topsheet and backsheet may be shaped to form a pant-like garment. In other cases, the topsheet, backsheet and absorbent core may be formed as a discrete assembly that is placed on a main chassis layer and the chassis layer is shaped to form a pant-like garment. The garment may be provided to the consumer in the fully assembled pant-like shape, or may be partially pant-like and require the consumer to take the final steps necessary to form the final pant-like shape, such as by fastening one or more fastener tabs. In the case of training pant-type garments and most adult incontinent products, the garment often is provided fully formed with factory-made side seams and the garment is donned by pulling it up the wearer's legs. In the case of diapers, a caregiver usually wraps the diaper around the wearer's waist and joins the side seams manually by attaching one or more fastener tabs, thereby forming a pant-like structure. For clarity, the present invention is described herein only with reference to a diaper-type garment in which the topsheet, backsheet and absorbent core are assembled into a structure that forms a pant-like garment when secured on a wearer using fastening devices, although the invention may be used with any other type of absorbent garment that may benefit from the use or addition of fastener tabs.

A preferred embodiment of the present invention comprises a disposable absorbent garment 10 of the diaper type, such as shown, for example, in FIG. 1. With reference to FIG. 1, a diaper 10 according to a preferred embodiment is shown in a relaxed condition with the effects of the elastics removed for purposes of clarity in the description. The diaper 10 chassis generally has an hourglass shape. The chassis generally can be defined in terms of a front waist region 22, a back waist region 24, and a crotch region 26. Those skilled in the art will recognize that "front" and "back" are relative terms, and these regions may be transposed without departing from the scope of the present invention. Alternatively, the diaper chassis can be configured in a generally rectangular shape or in a "T" shape. The diaper preferably comprises a topsheet 2, a backsheet 4, which may be either a different size than the topsheet 2 or may be substantially coterminous with the topsheet 2, and an absorbent core 6 disposed between at least a portion of the topsheet 2 and backsheet 4. Throughout this description, the terms "topsheet" and "backsheet" denote the relationship of these materials or layers with respect to the absorbent core 6. It is understood that additional layers may be present between the absorbent core 6 and the topsheet 2 and backsheet 4, and that additional layers and other materials may be present on the side opposite the absorbent core 6 from either the topsheet 2 or the backsheet 4. A pair of leg openings 28a, 28b extend along at least a portion of the crotch region 26 and one or more pairs of leg elastics 8 (three pairs are shown in FIG. 1) may be disposed to extend adjacent to leg openings 28a, 28b. Of course, in other embodiments, the leg elastics 8 may be omitted altogether.

The diaper 10 generally has a longitudinal direction 100 that extends generally parallel to the front-to-back axis of a wearer, and a lateral direction 102 that extends generally parallel to the side-to-side axis of a wearer. The diaper generally is symmetrical about a longitudinal centerline 60, but also may have asymmetrical components or shapes. The terms "inboard" and "outboard," as used herein, refer to positions generally along the lateral direction 102, with "inboard" locations being located closer to the longitudinal centerline 60 than "outboard" locations. "Outward" and "inward" mean in an outboard or inboard direction, respectively.

The diaper may further include a front waist elastic system 30a, a back waist elastic system 30b, and a waste containment system in the form of waste containment flaps 12 (also known as unitary leg gathers or standing leg gathers). Waste containment flaps 12 (FIG. 2) preferably extend from the front waist region 22 to the back waist region 24 along opposite sides of the longitudinal center line 60 of the diaper 10, or alternatively only along a portion thereof. The front waist region 22 and rear waist region 24 preferably include ear portions 38, 40 extending outward from the leg openings 28a, 28b to provide the garment 10 with an hourglass shape.

A variety of backsheet and topsheet constructions and materials are available and known in the art, and the invention is not intended to be limited to any specific materials or constructions of these components. The backsheet 4 may be made from any suitable pliable liquid-impervious material known in the art. Typical backsheet materials include films of polyethylene, polypropylene, polyester, nylon, and polyvinyl chloride and blends of these materials. For example, the backsheet can be comprised of a pigmented polyethylene film having a thickness in the range of 0.02–0.04 mm. The moisture-pervious topsheet 2 can be made of any suitable relatively liquid-pervious material known in the art that permits passage of liquid therethrough. Non-woven topsheet materials are exemplary because such materials readily allow the passage of liquids to the underlying absorbent core 6. Examples of suitable topsheet materials include non-woven spunbond or carded webs of polypropylene, polyethylene, nylon, polyester and blends of these materials.

The backsheet 4 and the topsheet 2 preferably are "associated" " with one another. The term "associated" encompasses configurations whereby the topsheet 2 is directly joined to the backsheet 4 by affixing the topsheet 2 directly to the backsheet 4, and configurations whereby the topsheet 2 is indirectly joined to the backsheet 4 by affixing the topsheet 2 to intermediate members which in turn are affixed to the backsheet 4. While the backsheet 4 and topsheet 2 in the preferred embodiment have substantially the same dimensions, they may also have different dimensions.

In addition, the backsheet 4 may be covered with a fibrous, nonwoven fabric layer (not shown) such as is disclosed, for example, in U.S. Pat. No. 4,646,362, which is incorporated herein by reference in its entirety and in a manner consistent with the present invention. Materials for such a fibrous outer liner include a spun-bonded nonwoven web of synthetic fibers such as polypropylene, polyethylene or polyester fibers; a nonwoven web of cellulosic fibers, textile fibers such as rayon fibers, cotton and the like, or a blend of cellulosic and textile fibers; a spun-bonded nonwoven web of synthetic fibers such as polypropylene; polyethylene or polyester fibers mixed with cellulosic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulosic, pulp or textile fibers.

The backsheet 4 may comprise multiple panels, such as three panels wherein a central poly backsheet panel is positioned adjacent the absorbent core while outboard nonwoven breathable side backsheet panels are attached to the side edges of the central poly backsheet panel. The backsheet may also be formed from microporous poly coverstock for added breathability. In other embodiments, the backsheet may be a laminate of several sheets. The backsheet may further be treated to render it hydrophilic or hydrophobic, and may have one or more visual indicators associated with it, such as labels indicating the front or back of the diaper or other characters or colorations. The present invention is not limited to any particular backsheet 4 material or construction.

Figure 2:
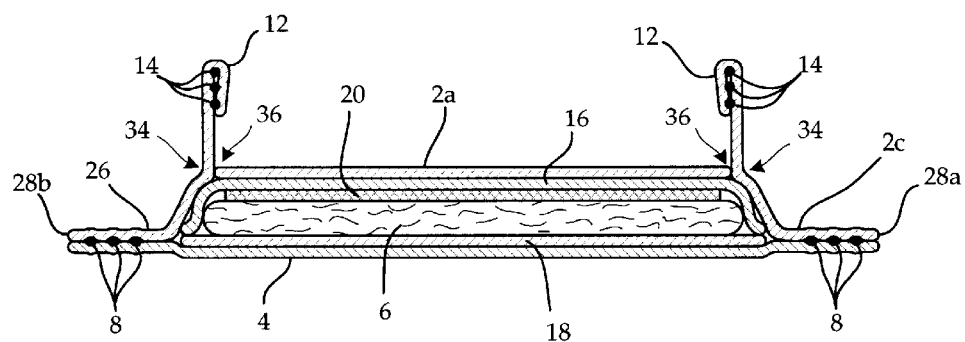
FIG. 2 is a cross-sectional view of a variation of the garment of FIG. 1, as viewed from reference line I—I, and shown having the additional layer located beneath, rather than above, the first tissue layer.

The topsheet 2 may be formed from one or more panels of material and may comprise a laminated sheet construction. In the embodiment of FIGS. 1 and 2, the topsheet comprises three separate portions or panels. A three-panel topsheet may comprise a central topsheet panel 2a that preferably is formed from a liquid-pervious material that is either hydrophobic or hydrophilic. The central topsheet panel 2a may be made from any number of materials, including synthetic fibers (e.g., polypropylene or polyester fibers), natural fibers (e.g., wood or cellulose), apertured plastic films, reticulated foams and porous foams to name a few. One preferred material for a central topsheet panel 2a is a cover stock of single ply non-woven material which may be made of carded fibers, either adhesively or thermally bonded, perforated plastic film, spunbonded fibers, or water entangled fibers, which generally weigh from 0.3–0.7 oz./yd$^2$ and have appropriate and effective machine direction and cross-machine direction strength suitable for use as a baby diaper cover stock material, as are known in the art. The central topsheet panel 2a preferably extends from substantially the front waist region 22 to the back waist region 24 or a portion thereof.

The second and third topsheet panels 2b, 2c in this embodiment may be positioned laterally outside of the central topsheet panel 2a. The outer topsheet panels 2b, 2c are preferably substantially liquid-impervious and hydrophobic, preferably at least in the crotch area. The outer edges of the outer topsheet panels may substantially follow the corresponding outer perimeter of the backsheet 4. The material for the outer topsheet portions or panels is preferably polypropylene and can be woven, non-woven, spunbonded, carded or the like, depending on the application.

An inner region 34 (FIG. 2) of the outer topsheet portions or panels 2b, 2c preferably are attached by, e.g., an adhesive, to the outer edges 36 of the inner topsheet portion or panel 2a. At the point of connection with the outer edges 36 of the inner topsheet portion or panel 2a, the inner regions 34 of the outer topsheet portions or panels 2b, 2c extend upwardly to form waste containment flaps 12. The waste containment flaps 12 may be formed of the same material as the outer topsheet portions or panels 2b, 2c, as in the embodiment shown. The waste containment flaps 12 may also be formed from separate elasticized strips of material that are associated with the topsheet, backsheet or both, or otherwise integrated into the garment. In another preferred embodiment, the topsheet 2 and backsheet 4 have similar dimensions or different dimensions, but in either case, the waste containment flaps 12 are attached to the topsheet 2 or to some intermediate element which in turn is attached to the topsheet 2.

The waste containment flaps 12 may be treated with a suitable surfactant to modify their hydrophobicity/hydrophilicity or imbued with skin wellness products as desired. The central topsheet portion or panel 2a may extend past the connection point with the waste containment flaps 12 and even extend to the periphery of the backsheet. Still further, the central topsheet portion or panel 2a could extend fully between the outer topsheet portions or panels 2b, 2c, and even beyond, so that the outer edges 36 of the central topsheet portion or panel 2a are coextensive with and sandwiched between the outer topsheet portions or panels 2b, 2c and the backsheet 4.

Each waste containment flap 12 preferably includes a portion that folds over onto itself to form an enclosure. One or more elastic members 14 (FIG. 2) may be secured in the enclosure in a stretched condition. As has been known at least as long as the disclosure of Tetsujiro, Japanese Patent document 40-11543, when the flap elastic 14 attempts to assume the relaxed, unstretched condition, the waste containment flaps 12 rise above the surface of the central topsheet portion or panel 2a. Various other configurations of topsheets 2 and waste containment systems, such as flaps 12, are known in the art, and the present invention is not intended to be limited to any particular design for these components.

The waist elastics 30a, 30b may be similar or different structures to impart similar or different elastic characteristics to the front and back waist portions 22, 24 of the diaper. In general, the waist elastics may comprise elastically extensible foam strips positioned at the front and back waist sections 22, 24. The foam strips preferably are about 0.50 inches to about 1.50 inches wide and about 3 inches to about 6 inches long. The foam strips preferably are positioned between the topsheet portions or panels and the backsheet 4. Alternatively, a plurality of elastic strands may be employed as waist elastics rather than foam strips. The foam strips preferably are polyurethane, but could be any other suitable material that preferably decreases waist band roll over, reduces leakage from the waist ends of the absorbent garment, and generally improves comfort and fit. The front and back waist foam strips 30a, 30b preferably are stretched to about 150% to about 250% of their unstretched length (in the lateral direction 102), and preferably to about 200% of their unstretched length, before being adhesively secured between the backsheet 4 and topsheet 2. Waist elastics are known in the art, and the present invention is not limited to the use of a particular waist elastic system, or to the inclusion of waist elastics at all.

Each leg opening 28a, 28b may be provided with a leg elastic containment system 8, sometimes referred to as conventional leg gathers. In a preferred embodiment, three strands of elastic threads are positioned to extend adjacent each leg openings 28a, 28b between the outer topsheet portions or panels 2b, 2c and the backsheet 4. The selection of appropriate elastics and the construction of leg elastic containment systems is known in the art. For example, the leg elastics 8 may be ultrasonically bonded, heat/pressure sealed using a variety of bonding patterns, or glued to the diaper 10.

Various commercially available materials may be used for the leg elastics 8 and elastic members 14, such as natural rubber, butyl rubber or other synthetic rubber, urethane, elastomeric materials such as spandex, which is marketed under various names, including LYCRA (DuPont), GLOSPAN (Globe) and SYSTEM 7000 (Fulflex), and so on. The present invention is not limited to any particular elastic material or to any particular shape, size or number of elastics.

The underlying structure beneath the topsheet 2 may include, depending on the absorbent garment construction, various combinations of elements, but in each embodiment, it is contemplated that the absorbent garment preferably will include an absorbent core 6. Although the absorbent core 6 depicted in FIG. 1 has a substantially rectangular shape as viewed in the plan view, other shapes may be used, such as a "T" shape or an hourglass shape. The absorbent core 6 may extend into either or both of the front and back waist regions 24, 22. The shape and construction of the absorbent core 6 may be selected to provide the greatest absorbency in target areas where body fluids are most likely to strike the diaper 10, which is often referred to as zoned absorbency. The absorbent core 6 may also comprise a number of layers of similar or different construction. The absorbent core may be associated with the topsheet 2, backsheet 4, or any other suitable part of the garment 10 by any method known in the art, in order to fix the absorbent core 6 in place.

Generally, in a preferred embodiment, the absorbent core 6 comprises particles of superabsorbent material (SAP) distributed within a fibrous structure. Additional fibrous or particulate additives may be disposed within the absorbent core 6 to add to the core's strength and SAP efficiency or to otherwise enhance the performance of the garment. The absorbent core 6 may be partially or wholly surrounded by a tissue layer 16, 18, and other additional layers 20 may be added to provide further benefits. For example, an additional layer 20 may be disposed between the topsheet 2 and absorbent core 6, as shown in FIG. 1, and/or other additional layers may be disposed between these layers, as shown in FIG. 2, or between absorbent core 6 and backsheet 4. The additional layer 20 or layers may comprise any useful layer known in the art or developed hereafter, such as a fluid acquisition layer, a distribution layer, an additional fibrous layer optionally containing superabsorbent particles (SAP), a wicking layer, a storage layer, or combinations and fragments of these layers. Such layers may be provided to assist with transferring fluids to the absorbent core 6, handling fluid surges, preventing rewet, containing absorbent material, improving core stability, or for other purposes. Skilled artisans are familiar with the various additional layers that may be included in absorbent articles, and the present invention is not intended to be limited to any particular type of materials used for those layers. Rather, the invention encompasses all types of wicking layers, all types of distribution layers, etc., to the extent that type of layer 20 is utilized.

The dimensions of the additional layer(s) 20 may be the same as or different from the dimensions of the absorbent core 6 and/or topsheet 2 and backsheet 4. It may be desirable to make the additional layers 20 smaller than the absorbent core 6 and located only where they are most needed, as such additional layers 20 may be relatively expensive.

The absorbent core 6 may be made from any absorbent material or materials, or combinations of such materials, known in the art or hereafter discovered. In one embodiment of the invention, the absorbent core 6 comprises wood fibers or other fibers such as chemical wood pulp, fibrous absorbent gelling material, or any other suitable liquid absorbing material, such as commercially available fluff pulp or fluffed bleached kraft softwood pulp or fibrous absorbent gelling material. In another embodiment of the invention, the absorbent core 6 comprises a combination of a porous fibrous web and superabsorbent particles. Absorbent cores are known in the art and exemplary cores are disclosed, for example, in U.S. Pat. No. 5,281,207 issued to Chmielewski et al., U.S. Pat. No. 4,610,678 issued to Weisman et. al., U.S. Pat. No. 5,137,537 issued to Herron et. al., U.S. Pat. No. 5,147,345 issued to Young et. al., U.S. Pat. No. 6,068,620 issued to Chmielewski, and U.S. Statutory Invention Registration No. H1,565, all of which are incorporated herein by reference in their entirety, and in a manner consistent with the present invention.

Preferably, the absorbent core is thin in order to improve the comfort and appearance of a garment. The importance of thin, comfortable garments is disclosed, for example, in U.S. Pat. No. 5,098,423 to Pieniak et al., which is incorporated herein by reference in its entirety and in a manner consistent with the present invention.

The absorbent core 6 preferably comprises a tissue wrapping that at least partially encloses the fibrous structure and SAP, such as disclosed in U.S. Pat. No. 6,068,620. The tissue wrapping is useful, for example, for containing the SAP within the absorbent core 6 and providing strength to the core during manufacturing and use. In a preferred embodiment, the tissue wrapping comprises first and second tissue layers 16, 18 that encase the absorbent core 6, and may optionally also encase one or more additional layers 20. Preferably, the first tissue layer 16 is located generally between the topsheet 2 and the absorbent core 6, and is hydrophilic and fluid pervious. It is also preferred that the second tissue layer 18 be located between the backsheet 4 and the absorbent core 6 and be hydrophobic and fluid impervious. The tissue wrapping may also comprise a single tissue layer that has been folded to encase the absorbent core, and that may be zone treated to render the portion that forms the lower tissue layer 18 hydrophobic and fluid impervious. The tissue layers 16, 18 or the whole core 6 may be crimped, folded, sealed or bonded to further help contain the fibrous structure and SAP particles.

The diaper 10 is fastened onto a wearer by using one or more, and preferably two, fastener tabs 32. The fastener tabs 32 preferably are affixed to the chassis of the diaper 10 to extend laterally outward (i.e., in the lateral direction 102) from a waist region 22, 24 of the garment. The fastener tabs 32 preferably are positioned to extend outward from the ear portions 40 of the rear waist region 24, but the fastener tabs 32 may also be attached to extend outward from the front waist region 22, or from both waist regions. The fastener tabs 32 may extend from one, but preferably both, lateral sides of the diaper 10. The fastener tabs 32 may be attached to any part of the diaper chassis, such as the topsheet 2, backsheet 4, outer covering or other layer of the diaper. The fastener tabs 32 may also be attached to either side of the diaper's chassis, to multiple layers of the chassis, or may be sandwiched between the various sheets comprising the chassis of the diaper 10. Variations on the number, location, and attachment configuration of the fastener tabs 32 will be apparent to those skilled in the art based on the teachings herein, and all such variations are within the scope of the present invention.

Figure 3:
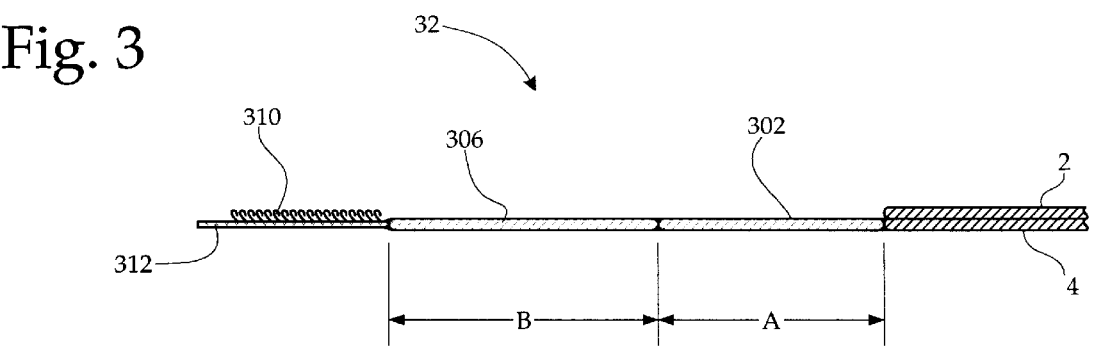
FIG. 3 is a cross-sectional view of a fastener tab according to a preferred embodiment of the present invention, showing a portion of an absorbent garment to which it is attached, as viewed from reference line II—II of FIG. 1.
Figure 4:
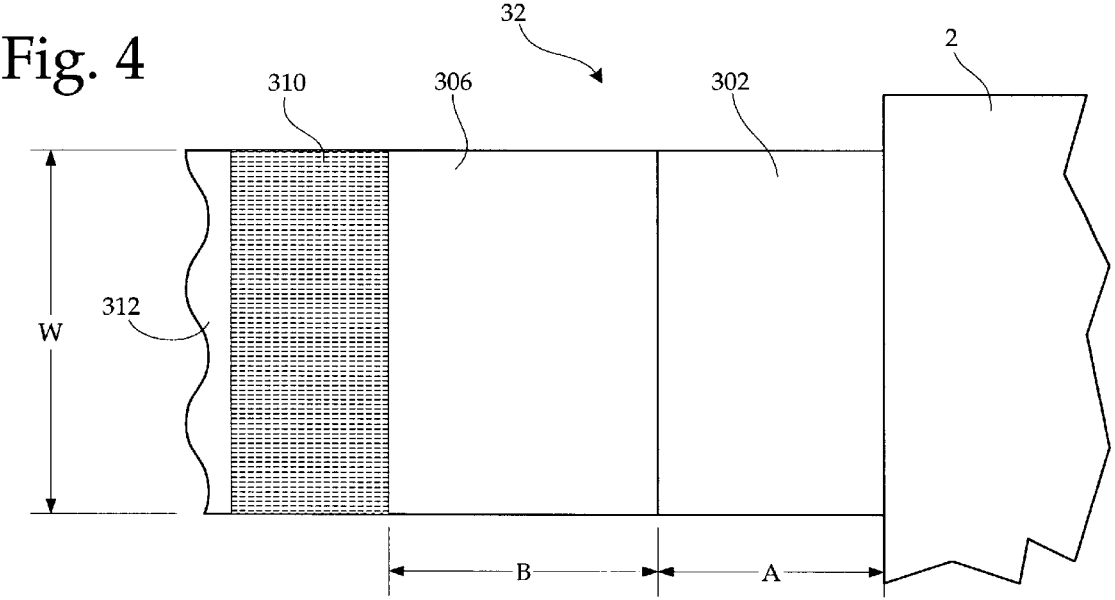
FIG. 4 is a plan view of the fastener tab of FIG. 3, showing a portion of an absorbent garment to which it is attached.

The fastener tabs 32 of the present invention are elasticized and have zones having different elastic properties to provide certain advantages over existing tab designs. FIGS. 3 and 4 depict edge and top views, respectively, of a first preferred embodiment of a fastener tab of the present invention. In a first preferred embodiment, the fastener tab 32 has a first elastic region 302 extending laterally outward from the diaper chassis and a second elastic region 306 located laterally outboard of the first elastic region 302. The second elastic region 306 may be an extension of the first elastic region 302 or may be a separate entity that is joined to the first elastic region 302. A grip 310 is attached, either directly or indirectly, at or near an outboard portion of the second elastic region 306, and the outermost extent of the fastener tab 32 may comprise a lifting region 312 that is adapted to allow the grip 310 to be lifted more easily. The grip 310 may also extend beyond a laterally outboard edge of the second elastic region 306, and there may be a substantially inelastic region or another elastic region (not shown) between the grip 310 and the second elastic region 306. Of course, other elasticized regions may be interposed between the various parts that have been described herein.

The grip 310 may comprise any hook-and-loop type fastener, adhesive fastener, or other type of fastener that is capable of holding the diaper 10 on a wearer. Suitable hook-and-loop fasteners are readily available from 3M Corp. (St. Paul, Minn.), Aplix, Inc. (Charlotte, N.C.), and Velcro USA, Inc. (Manchester, N.H.). Adhesive fasteners are also readily available, and disclosed, for example, in U.S. Pat. No. 4,645,501 issued to Teed, which is incorporated herein by reference in its entirety and in a manner consistent with the present invention. Suitable grips 310 of these and other types are generally known in the art, and the present invention is not limited to the use of any particular type of grip 310.

The grip 310 operates by engaging with or adhering to a corresponding surface or object (not shown) located on the opposite end of the diaper 10, and preferably in the opposite waist region as the fastener tabs 32. In those cases in which a hook-and-loop type fastening system is used, the hook portion of the system preferably is used as the grip 310, and the loop portion preferably is affixed to or contained within the outer surface of the diaper 10 at the end opposite the fastener tabs 32. An integral portion of the diaper 10, such as the backsheet 4 or an outer covering, also may be adapted to serve as the loop portion or other object to which the grip 310 attaches, either in its normal state or after being treated to better engage with the grip 310. The design and selection of a surface or object to which the grip 310 fastens or attaches is known in the art, and the present invention is not limited to the use of any particular device or construction for these parts.

The first and second elastic regions 302, 306 may comprise any structure that is elastically extensible, and may have similar or dissimilar constructions, provided they may be joined to one another and to a diaper 10 and a grip 310, respectively, to adequately handle the usage loads. The terms "elastic," "elastically extensible," and variations of these terms as used herein, are understood by those skilled in the art, and generally refer to the ability of a material or combination of materials (such as an aggregate or laminate), to be extended and retracted with little or no plastic deformation, yielding or rupturing (except as explained elsewhere) of the various parts of the material or combination of materials. The term "inelastic" and variations thereof as used herein, are understood by those skilled in the art, and generally refer to the substantial absence of elastic properties. Other meanings of these terms will be clear to those skilled in the art of absorbent garment construction.

In a preferred embodiment, the first and second elastic regions 302, 306 comprise elastic laminates having one or more elastic layers bonded to one another or to one or more inelastic layers. A preferred elastic laminate comprises an elastic layer disposed between a pair of inelastic layers. The elastic layer preferably comprises a styrene based elastic film, such as those disclosed in U.S. Pat. No. 6,313,372 issued to Suzuki, which is incorporated herein by reference in its entirety and in a manner consistent with the present invention, however the elastic may also be another type of elastic film, a multidirectional elastic aggregate such as elastic webbing, netting, or scrim elastic, foam, strands or bands of suitable elastic materials, such as natural or synthetic rubber, urethane elastomers, spandex, LYCRA and elastic polymers. Other suitable elastics will be apparent to those skilled in the art in light of the present teachings. The elastic layer for an elastic laminate typically is stretched then affixed between a pair of inelastic layers, which then contract when the elastic layer contracts. In some cases, however, the elastic layer may be affixed between the inelastic layers while in a relaxed state, such as when the elastic layer is a heat-activated material that elastically contracts after being heated. The inelastic outer layers preferably comprise a nonwoven material, such as a spunbonded polypropylene or polyethylene nonwoven similar to those used for the topsheet 2, but may also be any suitable material that encases the elastic layer, protects the elastic layer, allows slideable contact between the elastic regions 302, 306 and other parts of the diaper 10, or prevents such sliding, protects the wearer from uncomfortable exposure to the elastic layer or provides other benefits. Other uses for the outer layer or layers will be apparent to those skilled in the art based on the teachings herein. In a preferred embodiment, the first and second elastic regions 302, 306 are breathable to provide additional comfort to the wearer, i.e., the first and second elastic regions 302, 306 have a moisture vapor transmission rate (MVTR) of at least 250 grams/(m² 24 hours), and more preferably an MVTR of about 750 grams/(m² 24 hours), and most preferably an MVTR of about 1500 grams/(m² 24 hours). The measurement of moisture vapor transmission rate is explained in U.S. Pat. No. 5,879,34 to Odorzynski, which is incorporated by reference herein in its entirety and in a manner consistent with the present invention. Preferred elastic laminates that are suitable for use with the present invention are FABRIFLEX 204 and FABRIFLEX 304 available from Tredegar Film Products of Richmond, Va.

The bonding between the various layers of a preferred elastic laminate preferably is accomplished using a number of heat bonds or ultrasonic bonds, but may also be accomplished using adhesives, combinations of different bonding methods, or any other joining method known in the art or later developed. The construction of such elastic laminates is known in the art, and a skilled artisan will be able to provide a suitable elastic laminate or other elastic design for the first and second elastic regions 302, 306 without undue experimentation, based on the teachings provided herein.

One or both of the elastic regions 302, 306 may also be a "zero strain" stretch-laminate, which generally is manufactured by attaching a sheet of elastic to outer layers while the elastic is in a relaxed state, then "activating" the laminate by extending the elastic to create plastic deformation, yielding or rupturing in the outer layers. After the initial activation, the zero-strain stretch laminate behaves generally like any other elastic laminate. Such elastics are disclosed, for example, in U.S. Pat. No. 5,464,401 issued to Hasse et al., and U.S. Pat. No. 6,313,372 issued to Suzuki, which are incorporated herein by reference in their entirety and in a manner consistent with the present invention. One or both of the elastic regions 302, 306 may also comprise sheets, ribbons, scrims, strands, foams or other types of elastic material that may or may not be secured between outer sheets. Still another material that may be used for one or both of the elastic regions 302, 306 is a coextruded sheet of elastic and inelastic polymers, such as is disclosed, for example, in U.S. Pat. No. 4,787,897 issued to Torimae et al., which is incorporated herein by reference in its entirety and in a manner consistent with the present invention.

The elastic regions 302,306 may be joined to one another, to the grip 310 and to the diaper chassis by any method known in the art. Exemplary joining methods include, but are not limited to, ultrasonic bonding, heat bonding, adhesive bonding, chemical bonding, and so on. Of these, heat bonding, ultrasonic bonding and adhesive bonding, and combinations of these bonding methods are preferred. Additional substrate layers may also be added to the elastic regions 302, 306 to facilitate their bonding with the diaper chassis and grip 310. The first and second elastic regions 302, 306 may also be manufactured as a single unit having varying elastic properties so that it is not necessary to bond these two regions to one another.

Figure 5:
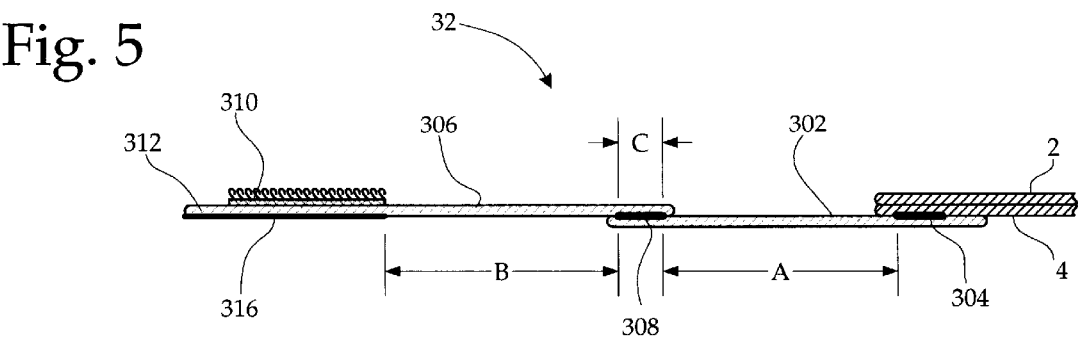
FIG. 5 is a cross-sectional view of a fastener tab according to another preferred embodiment of the present invention, showing a portion of an absorbent garment to which it is attached, as viewed from reference line II—II of FIG. 1.
Figure 6:
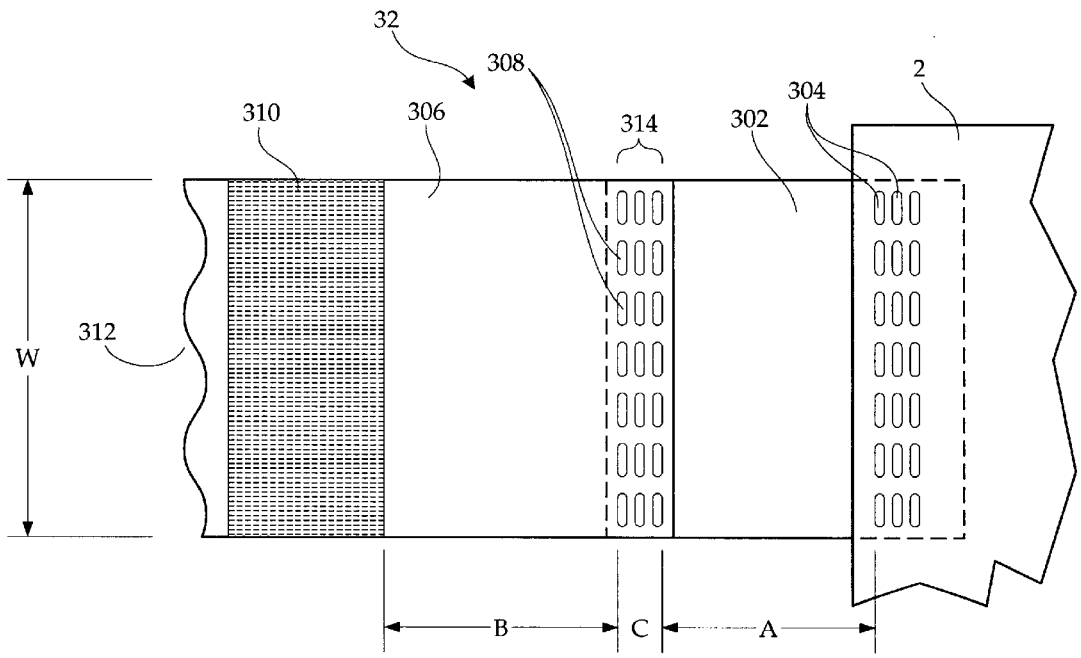
FIG. 6 is a plan view of the fastener tab of FIG. 5, showing a portion of an absorbent garment to which it is attached.

Referring now to FIGS. 5 and 6, a fastener tab 32 according to a second preferred embodiment of the present invention is shown. In the second preferred embodiment, the first elastic region 302 partially overlaps the diaper chassis, and is joined to the diaper chassis in this overlapping region by one or more chassis bonds 304, which may be accomplished by any suitable method, such as those described elsewhere herein. Similarly, the second elastic region 306 partially overlaps the first elastic region 302 (either elastic region 302, 306 may be positioned to face the wearer) and the two are joined by one or more tab bonds 308, which also may be made using any suitable bonding method, such as those described elsewhere herein. Also in the second preferred embodiment, the grip 310 is joined to or integrally formed with the surface of the second elastic region 306. It has been found that in those cases in which the grip 310 is relatively inelastic, an additional inelastic layer 316, such as an inelastic film, may be affixed to the portion of the second inelastic region 306 that underlies the grip 310 to provide a better bond between the grip 310 and the second inelastic region 306. The additional inelastic layer 316 may also extend into the lifting region 312 so that the lifting region does not contract, making the lifting region 312 easier to use. A variety of bonding patterns may be used to join the various parts, as will be understood by those skilled in the art.

The various parts of the fastener tab 32 preferably have approximately the same width W (as measured in the longitudinal direction 100) and have parallel sides that extend substantially parallel (within about 5 degrees) to the lateral direction 102 of the garment 102. However, it may be desirable for the various parts to have varying widths, and the sides may extend at an angle relative to the lateral direction 102. Such variations will be apparent to those skilled in the art based on the teachings herein, and are within the scope of the present invention.

In both the first and second preferred embodiments, the first elastic region 302 has a relaxed length A, and the second elastic region has a relaxed length B. In the second preferred embodiment, there is a central region 314 (FIG. 6) having a length C, where the first and second elastic regions 302, 306 overlap. (The lengths of the first and second elastic regions 302, 306 and the central region are measured in the lateral direction 102.) When the first and second elastic regions 302, 306 overlap, their relaxed and unrelaxed lengths are measured as the portion of each elastic region that is between the nearest bonds, so for the first elastic region 302 the length A is measured between the nearest of the chassis bonds 304 and tab bonds 308, and for the second elastic region 306 the length B is measured between the nearest of the tab bonds 308 and the grip 310 or the additional inelastic layer 316, whichever is closer.

In the second preferred embodiment, the tab bonds 308 may or may not affect the elastic properties of the first and second elastic regions 302, 306. In one preferred embodiment, the tab bonds 308 substantially reduce the elasticity of both the first and second elastic regions 302, 308, thereby causing the central region 314 to be substantially inelastic. Heat and ultrasonic bonding methods, which may be used in combination with one another and in combination with adhesive bonding, are preferred for making the tab bonds 308 such that they make the central region 314 substantially inelastic. In other embodiments, the rigidity (stretching resistance) of the first and second elastic regions 302, 306 will be combined in the central region 314 to increase the rigidity of that region. The degree to which the rigidity of the first and second regions 302, 306 are combined depends on the manner in which the two regions are joined, as will be understood by those skilled in the art.

Numerous benefits may be obtained by providing the first and second elastic regions 302, 306 with different elastic properties. In each of the preferred embodiments of the present invention, these benefits are provided when the first elastic region 302 has a greater stretch resistance than the second elastic region 306. The "stretch resistance" as understood herein, is a relative determination of how much a given length of a particular region will stretch when subjected to a given tensile force. Regions having a greater stretch resistance will extend less than those having a lesser stretch resistance when the same tensile force is applied to each. The stretch resistance of each elastic regions may be varied by modifying a number of variables. For example, the modulus of elasticity of the elastic material may be increased to increase the stretch resistance. Also, the width W or thickness (i.e., cross-sectional area) of the elastic regions 302, 306 may be increased to increase their stretching resistance. These and other ways of modifying the stretch resistance of each elastic region 302, 306 and the central region 314 will be understood by those skilled in the art based on the teachings provided herein.

Figure 7:
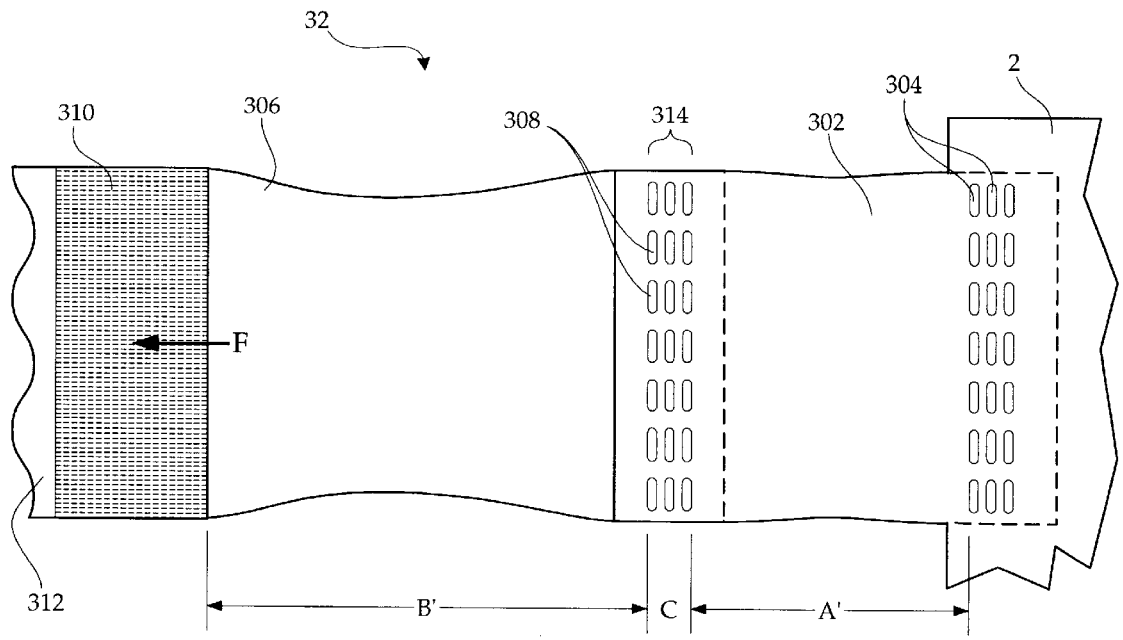
FIG. 7 is a plan view of the fastener tab of FIG. 5, shown under a lateral tensile force.

Referring now to FIG. 7, when a tensile force F is applied to the grip 310 in the lateral direction 102, the first region 302 and second region 306 elastically extend. The first region's extended length is shown as dimension A', and the second region's extended length is shown as dimension B'. In the embodiment of FIG. 7, the central region 314 is relatively inelastic, so its extended length is essentially equal to its contracted length C. The change in length of each elastic region 302, 306 caused by the tensile force F may be described in a general sense by simple spring equations (such as Hooke's Law and derivations thereof). According to the preferred embodiments, the first elastic region 302 has a higher stretch resistance than the second elastic region 306, and so the proportional difference in length of the first elastic region 302 (as measured by the equation (A'−A)/A) is less than the proportional difference in length of the second elastic region 306 (as measured by the equation (B'−B)/B) for any given tensile force F.

Figure 8:
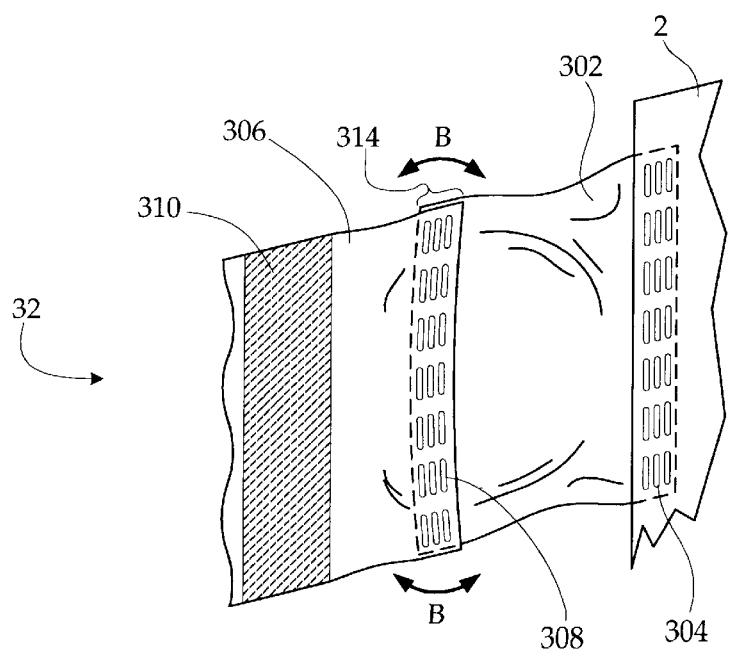
FIG. 8 is a plan view of the fastener tab of FIG. 5, shown under a lateral tensile force and a vertical force.

Referring now to FIG. 8, one advantage of the preferred embodiments is that it allows longer fastener tabs 32 to be used without some of the disadvantages normally associated with relatively long and relatively pliable tabs. Fastener tabs 32, particularly those that are long or pliable (i.e., having a low bending stiffness), are subject to folding over or curling during use. Curling occurs for a variety of reasons. For example, curling may occur when the tab is pinched between a wearer's body parts, such as the leg and waist, when the wearer moves. Once the tab is folded, the tensile forces on it that hold the diaper to the wearer become even more concentrated and may pull the fastener tab into folds in the wearer's body, causing discomfort and possibly irritation and redness. The relatively rigid attachment points between the tab and the front and rear waist regions assist to hold the ends of the tab in an unfolded position, but do little to prevent the middle of the tab from curling, particularly when the tab is relatively long or flexible.

As can be seen in FIG. 8, a fastener tab 32 constructed according to a preferred embodiment of the present invention may reduce or prevent tab folding or curling, particularly in the middle portions of the tab. The central region 314 of one preferred embodiment comprises a laminate of portions of the first elastic region 302 and the second elastic region 306. When these layers are bonded to one another their bending stiffness increases (this is sometimes referred to as the "plywood effect"). When bending forces B are applied to the middle of the fastener tab 32, the increased bending stiffness of the central region 314 resists these bending forces B more than either of the elastic regions 302, 306 would if they were acting alone. The lengths of the elastic regions and the amount of overlap may be selected to position and size the central region 314 to improve the fastener tab's resistance to curling or folding.

Another advantage of a fastener tabs 32 according to a preferred embodiment is that it provides the diaper 10 with an improved fit and aesthetic appearance, particularly in the waist region 22, 24 to which the first elastic region 302 is attached. Referring now to FIGS. 9 and 10, the diaper tabs 32 typically are subjected to a tensile force F that is applied to constrict the diaper 10 around the wearer's waist. In addition to the tensile force F, the relative shifting of the front and rear waist regions 22, 24 tends to place a vertical load L on the fastener tabs 32. The front and rear waist regions 22, 24 of the diaper 10 often shift vertically relative to one another to create such a vertical load L when the wearer moves, when the diaper 10 becomes loaded with exudates and under a variety of other circumstances.

As shown in FIG. 9, which depicts a conventional prior art tab 932 under a tensile force F and a vertical load L, conventional tabs 932 tend to deform as these loads are applied. In particular, one or more diagonal folds 902 sometimes extend from the lower edge of the grip 310 to the opposite corner of the tab 932. Despite the presence of chassis bonds 304 between the conventional tab 932 and the chassis, the fold or folds in the conventional tab 932 are often conveyed directly to the diaper chassis in the ear portion 40 and beyond. As a result, both the conventional tabs 932 and the diaper chassis become folded. This folding may lead to reduced comfort, as the tensile force F and vertical load L tend to become more concentrated in the valleys of the folds, thereby pressing harder against the wearer. In addition, the folding of the tab and diaper chassis may reduce leakage protection. Still further, the folding leads to reduced aesthetic appeal of the ears 40, which preferably have a smooth and neat appearance.

Referring now to FIG. 10, the present invention uses the relatively rigid first elastic region 302 to improve the wrinkle resistance and aesthetic appeal of the diaper 10. The distortion of the fastener tab 32 caused by the lateral force F and the vertical load L tend to be reduced when the first elastic region 302 has a higher stretch resistance than the second elastic region 306. This is possibly the result of a more homogeneous stress distribution caused by the combination of these two regions. This may also follow from the additional stiffness provided by tab bonds 308 in the central region 314 of the fastener tab 32. Generally, as is illustrated in FIG. 10, when a tensile force F and vertical load L are placed on a fastener tab 32 of a preferred embodiment, these forces result in a more uniform distortion of the various parts, and large diagonal folds 902 are reduced and replaced by smaller redistributed distortions 1002 that have less impact on the aesthetic appeal than the large distortions associated with conventional tabs 432. This additional smoothness, particularly around the ear portion 40, may also improve the diaper's leakage resistance by reducing the number of channels and folds through which migrating bowel movement or urine may pass.

Yet another advantage of the preferred embodiments of the present invention is that the first elastic region 302 may not irritate the wearer as much as with conventional relatively long diaper tabs 932. The diaper chassis is often designed so that the front and rear ear portions 38, 40 overlap one another during use, thereby acting as a barrier between the fastener tabs 32 and the wearer's body. Long diaper tabs 932 present a problem because they allow greater flexibility between the front and rear waist region 22, 24, and so the front and rear ear portions 38, 40 may move relative to one another and become folded, doubled over, or otherwise move so that the fastener tabs 32 are in direct contact with the wearer's skin. This contact may lead to discomfort, redness and irritation as the tab expands and contracts against the wearer's skin.

The use of a first elastic region 302 having a relatively high stretch resistance helps prevent the amount of ear folding that the diaper experiences, and reduces wearer discomfort when such folding occurs. In a preferred embodiment, the fastener tab's elastic properties are concentrated in the second elastic region 306, and the first elastic region 302 generally experiences less deformation during use. The reduced deformation in the first elastic region 302 tends to fold, crease, or otherwise manipulate the ear portions 38, 40 less than conventional elastic tabs, thereby reducing the likelihood that these parts will fold during use. Furthermore, even if the ear portions 38, 40 fold, or the wearer is otherwise exposed to direct contact with the fastener tabs, it is likely that such contact will be with the first elastic region 302 (at least to begin with), and the degree of discomfort will be reduced because the first elastic region 302 does not stretch and contract as much as conventional long elastic tabs, thereby reducing differential movement between the first elastic region 302 and the wearer's skin.

Still another benefit of the preferred embodiments of the present invention is that they provide the caregiver with a greater impression of security of the garment's attachment. Caregivers typically associate increased stretch with improved fit. In most garments, however, the stretch for the waist encircling portion is provided by using waist elastics 30a, 30b, which are positioned behind the back of the wearer, and thus out of the caregiver's sight, during attachment of the tabs to the diaper 10. As such, the caregiver receives little visual input as to the state of relaxation or extension of the waist elastics 30a, 30b. By providing second elastic regions 306 having relatively low stretch resistance, the present invention provides a visible and tangible expansion of the diaper elastics, leading to an improved ability to control the fit of the diaper 10. Conventional waist elastics 30a, 30b may even be unnecessary in such an embodiment due to the additional stretch provided in the second waist region 306.

In a particularly preferred embodiment, the fastener tab 32 comprises a first elastic region 302, second elastic region 306 and a central region 314. In the central region 314, the first and second elastic regions 302, 306 overlap and are joined by tab bonds 308 made by ultrasonic bonding, heat bonding, adhesive bonding or a combination of these techniques, to make the central region 314 substantially inelastic. Each of the first and second elastic regions 302, 306 comprises an elastic laminate having a styrene based elastic film as the internal elastic layer, and nonwoven outer layers. A grip 310 is affixed to one side of the second elastic region 306, and an additional layer 316 of substantially inelastic plastic film is attached to the portion of the second elastic region 306 that underlies the grip 310. The additional layer 316 and second elastic region extend outboard of the grip 310 to form a lifting region 312. The grip 310 comprises the hook portion of a hook-and-loop fastening system.

Figure 13:
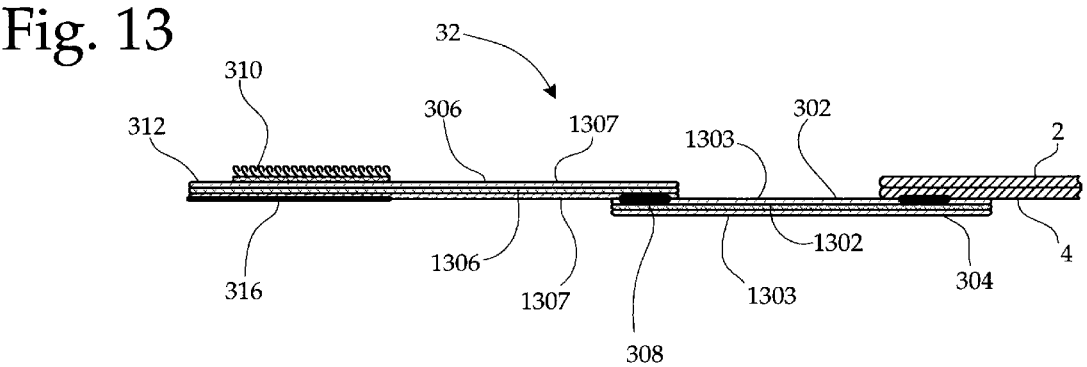
FIG. 13 is a cross-sectional view of a fastener tab according to yet another preferred embodiment of the present invention, showing a portion of an absorbent garment to which it is attached, as viewed from reference line II—II of FIG. 1.

One or both of the first and second elastic regions 302, 306 may comprise an elastic laminate. For example, in FIG. 13, the first elastic region 302 comprises an elastic laminate having a central elastic layer 1302 disposed between two inelastic layers 1303, and the second elastic region 306 comprises an elastic laminate having a central elastic layer 1306 disposed between two inelastic layers 1307.

In a preferred embodiment the first elastic region 302, second elastic region 306, central region 314, grip 310 and lifting region 312 are approximately the same width. Preferably the fastener tab 32 has a width W of about 25 millimeters (mm) to about 115 mm, and more preferably of about 45 to about 95 mm, and most preferably of about 70 mm. Also in a preferred embodiment, the first elastic region 302 has a relaxed length A of about 10 mm to about 70 mm, and more preferably of about 18 mm to about 50 mm, and most preferably of about 25 mm to about 30 mm. The second elastic region 306 of a preferred embodiment has a length B of about 10 mm to about 85 mm, and more preferably of about 20 mm to about 60 mm, and most preferably of about 30 mm to about 35 mm. The central region 314 of a preferred embodiment has a length C of about 3 mm to about 40 mm, and more preferably of about 5 mm to about 25 mm, and most preferably of about 10 mm.

The tab bonds 308 preferably are circular, ovate, rectangular or similarly shaped, each having a long axis dimension of up to about 4 mm, and a short axis dimension of about 3 mm or less, but any other suitable pattern may be used. Any suitably sized grip 310 may be used, and in a preferred embodiment the grip 310 has a length in the lateral direction 102 of about 5 mm to about 30 mm, and more preferably of about 10 mm to about 25 mm, and most preferably of about 15 mm.

The fastener tab 32 preferably may be elastically extended such that the first elastic region 302 has an extended length A' of about 20 mm to about 75 mm, and more preferably of about 25 mm to about 60 mm, and most preferably of about 35 mm to about 40 mm. The second elastic region 306 preferably may be extended to a length of about 20 mm to about 100 mm, and more preferably of about 40 mm to about 80 mm, and most preferably of about 60 mm to about 65 mm.

In a preferred embodiment, when a lateral tensile force is applied to the grip 310 to extend the first elastic region 302 to about 110% to about 180% of its original length, the second elastic region 306 will be extended to about 160% to about 230% of its original length. In a more preferred embodiment, when a lateral tensile force is applied to the grip 310 to extend the first elastic region 302 to about 130% to about 160% of its original length, the second elastic region 306 will be extended to about 175% to about 215% of its original length. In a most preferred embodiment, when a lateral tensile force is applied to the grip 310 to extend the first elastic region 302 to about 145% of its original length, the second elastic region 306 will be extended to about 195% of its original length.

Figure 11:
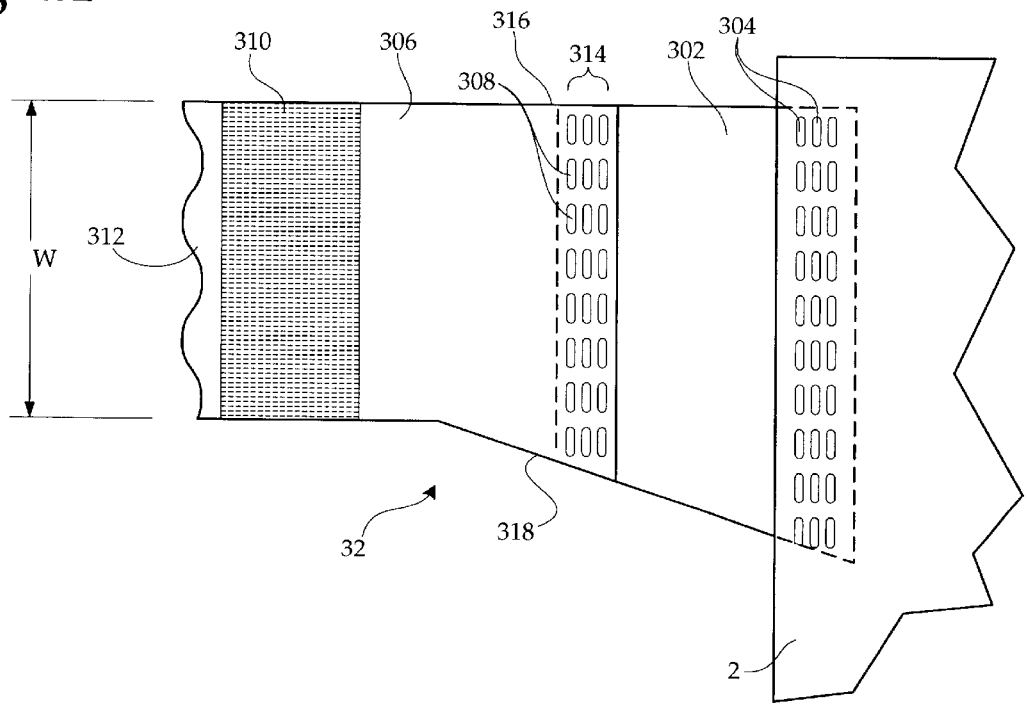
FIG. 11 is a plan view of a fastener tab having non-parallel side edges according to another preferred embodiment of the present invention.
Figure 12:
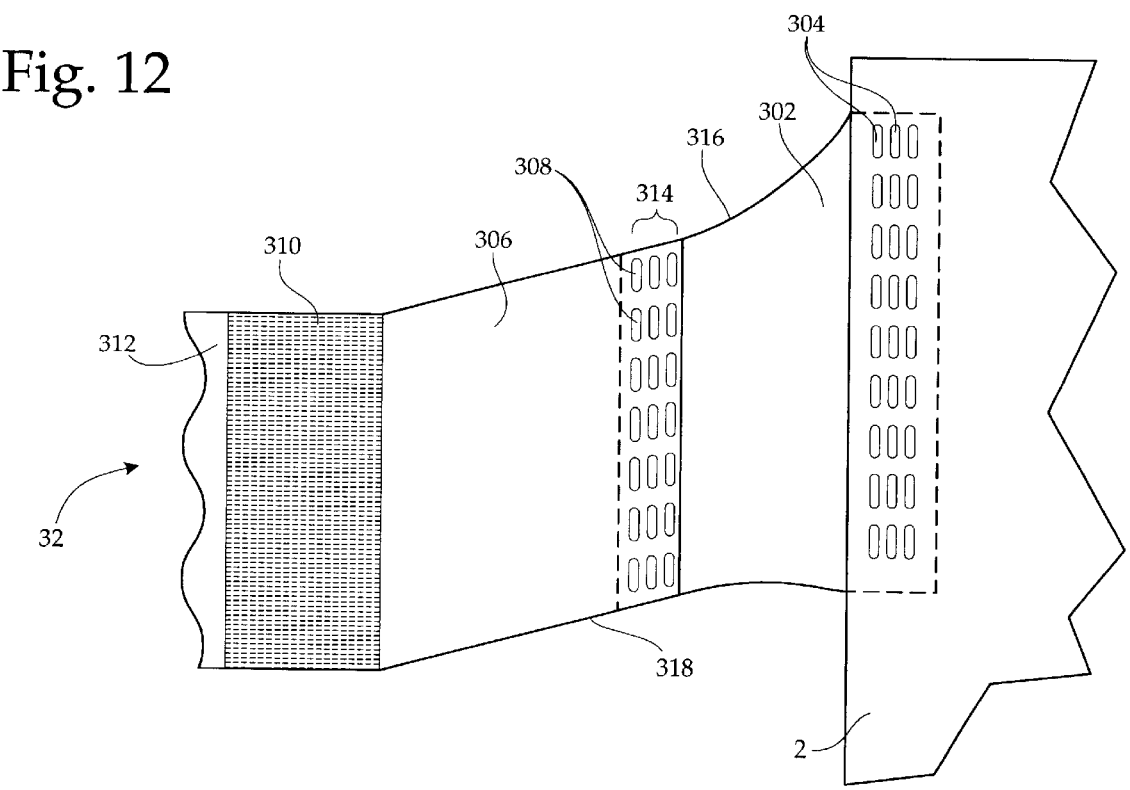
FIG. 12 is a plan view of another fastener tab having non-parallel side edges according to another preferred embodiment of the present invention.

Referring now to FIGS. 11 and 12, other benefits may be obtained by providing the fastener tab 32 of a preferred embodiment with non-parallel top and bottom side edges 316, 318. The top edge 316 and bottom edge 318 define the laterally extending extents of the fastener tab 32. It may be desirable to angle or contour one or both of the top and bottom side edges 316, 318 relative to one another to provide improved fit, leakage protection, aesthetic appeal, or other benefits. These and other benefits of non-parallel side edges are disclosed, for example, in U.S. Pat. No. 5,496,298 to Kuepper et al., which is incorporated by reference herein in its entirety and in a manner consistent with the present invention.

Non-parallel side edges 316, 318 may have a linear or arcuate shape or a combination thereof. The non-parallel portions of the side edges 316, 318 may also terminate in the first elastic region 302, the second elastic region 306, the central region 314, the grip 310, or any other part of the fastener tab 32 such that portions the side edges 316, 318 may be parallel with one another. If the side edges 316, 318 are non-parallel, they may be oriented so that the fastener tabs 32 is wider where it is attached to the diaper chassis, where it is attached to the grip 310, or at some intermediate location, such as at the central region 314.

Referring to FIG. 12, both side edges 316, 318 may also be angled or curved in the same general direction relative to the lateral direction 102 such that the grip 310 is offset in the longitudinal direction 100 relative to the attachment between the first elastic region 302 and the diaper chassis. In such an embodiment, all or part of the side edges 316, 318 may be non-parallel or parallel. Other variations of angled and non-parallel side edge configurations will be apparent to those skilled in the art based on the teachings provided herein.

Other embodiments, uses, and advantages of the invention will be apparent to those skilled in the art from consideration of the specification and practice of the invention disclosed herein. The specification should be considered exemplary only, and the scope of the invention is accordingly intended to be limited only by the following claims and equivalents thereof.

I claim:

1. A fastener tab for an absorbent garment having longitudinally opposite waist regions when laid flat, the fastener tab comprising:
    a first elastic region adapted to be attached to an absorbent garment to extend laterally outwardly from a waist region thereof;
    a second elastic region extending laterally outward from the first elastic region;
    a grip attached to an outboard portion of the second elastic region;
    wherein the first elastic region has a greater stretch resistance than the second elastic region; and
    wherein when a lateral tensile force is applied to the grip to extend the first elastic region to a length of about 110% to about 180% of its original length, the second elastic region is extended to a length of about 160% to about 230% of its original length.

2. The fastener tab of claim 1, further comprising a lifting region extending laterally outward from the grip.

3. The fastener tab of claim 1, wherein at least one of the first elastic region and the second elastic region comprises an elastic laminate having a central elastic layer disposed between inelastic layers.

4. The fastener tab of claim 1, wherein the grip comprises the hook portion of a hook-and-loop fastener.

5. The fastener tab of claim 1, wherein the grip comprises an adhesive fastener.

6. The fastener tab of claim 1, wherein the first elastic region, second elastic region and grip have approximately the same width.

7. The fastener tab of claim 1, wherein the fastener tab has a width of about 25 millimeters (mm) to about 115 mm.

8. The fastener tab of claim 1, wherein the fastener tab has a width of about 45 mm to about 95 mm.

9. The fastener tab of claim 1, wherein the fastener tab has a width of about 70 mm.

10. The fastener tab of claim 1, wherein the first elastic region has a relaxed length of about 10 mm to about 70 mm.

11. The fastener tab of claim 1, wherein the first elastic region has a relaxed length of about 18 mm to about 50 mm.

12. The fastener tab of claim 1, wherein the first elastic region has a relaxed length of about 25 mm to about 30 mm.

13. The fastener tab of claim 1, wherein the second elastic region has a relaxed length of about 10 mm to about 85 mm.

14. The fastener tab of claim 1, wherein the second elastic region has a relaxed length of about 20 mm to about 60 mm.

15. The fastener tab of claim 1, wherein the second elastic region has a relaxed length of about 30 mm to about 35 mm.

16. The fastener tab of claim 1, wherein the first elastic region may be elastically extended to a length of about 20 mm to about 75 mm.

17. The fastener tab of claim 1, wherein the first elastic region may be elastically extended to a length of about 25 mm to about 60 mm.

18. The fastener tab of claim 1, wherein the first elastic region may be elastically extended to a length of about 35 mm to about 40 mm.

19. The fastener tab of claim 1, wherein the second elastic region may be elastically extended to a length of about 20 mm to about 100 mm.

20. The fastener tab of claim 1, wherein the second elastic region may be elastically extended to a length of about 40 mm to about 80 mm.

21. The fastener tab of claim 1, wherein the second elastic region may be elastically extended to a length of about 60 mm to about 65 mm.

22. The fastener tab of claim 1, wherein when a lateral tensile force is applied to the grip to extend the first elastic region to a length of about 130% to about 160% of its original length, the second elastic region is extended to a length of about 175% to about 215% of its original length.

23. The fastener tab of claim 1, wherein when a lateral tensile force is applied to the grip to extend the first elastic region to a length of about 145% of its original length, the second elastic region is extended to a length of about 195% of its original length.

24. The fastener tab of claim 1, wherein the fastener tab has non-parallel side edges.

25. A fastener tab for an absorbent garment having longitudinally opposite waist regions when laid flat, the fastener tab comprising:
    a first elastic region adapted to be attached to an absorbent garment to extend laterally outwardly from a waist region thereof;
    a substantially inelastic region extending laterally outward from the first elastic region;
    a second elastic region extending laterally outward from the substantially inelastic region;
    a grip attached to an outboard portion of the second elastic region;
    wherein the first elastic region has a greater stretch resistance than the second elastic region; and
    wherein when a lateral tensile force is applied to the grip to extend the first elastic region to a length of about 110% to about 180% of its original length, the second elastic region is extended to a length of about 160% to about 230% of its original length.

26. The fastener tab of claim 25, further comprising a lifting region extending laterally outward from the grip.

27. The fastener tab of claim 25, wherein at least one of the first elastic region and the second elastic region comprises an elastic laminate having a central elastic layer disposed between inelastic layers.

28. The fastener tab of claim 25, wherein the grip comprises the hook portion of a hook-and-loop fastener.

29. The fastener tab of claim 25, wherein the grip comprises an adhesive fastener.

30. The fastener tab of claim 25, wherein the first elastic region, second elastic region, substantially inelastic region and grip have approximately the same width.

31. The fastener tab of claim 25, wherein the fastener tab has a width of about 25 millimeters (mm) to about 115 mm.

32. The fastener tab of claim 25, wherein the fastener tab has a width of about 45 mm to about 95 mm.

33. The fastener tab of claim 25, wherein the fastener tab has a width of about 70 mm.

34. The fastener tab of claim 25, wherein the first elastic region has a relaxed length of about 10 mm to about 70 mm.

35. The fastener tab of claim 25, wherein the first elastic region has a relaxed length of about 18 mm to about 50 mm.

36. The fastener tab of claim 25, wherein the first elastic region has a relaxed length of about 25 mm to about 30 mm.

37. The fastener tab of claim 25, wherein the second elastic region has a relaxed length of about 10 mm to about 85 mm.

38. The fastener tab of claim 25, wherein the second elastic region has a relaxed length of about 20 mm to about 60 mm.

39. The fastener tab of claim 25, wherein the second elastic region has a relaxed length of about 30 mm to about 35 mm.

40. The fastener tab of claim 25, wherein the first elastic region may be elastically extended to a length of about 20 mm to about 75 mm.

41. The fastener tab of claim 25, wherein the first elastic region may be elastically extended to a length of about 25 mm to about 60 mm.

42. The fastener tab of claim 25, wherein the first elastic region may be elastically extended to a length of about 35 mm to about 40 mm.

43. The fastener tab of claim 25, wherein the second elastic region may be elastically extended to a length of about 20 mm to about 100 mm.

44. The fastener tab of claim 25, wherein the second elastic region may be elastically extended to a length of about 40 mm to about 80 mm.

45. The fastener tab of claim 25, wherein the second elastic region may be elastically extended to a length of about 60 mm to about 65 mm.

46. The fastener tab of claim 25, wherein when a lateral tensile force is applied to the grip to extend the first elastic region to a length of about 130% to about 160% of its original length, the second elastic region is extended to a length of about 175% to about 215% of its original length.

47. The fastener tab of claim 25, wherein when a lateral tensile force is applied to the grip to extend the first elastic region to a length of about 145% of its original length, the second elastic region is extended to a length of about 195% of its original length.

48. The fastener tab of claim 25, wherein the substantially inelastic region has a length of about 3 mm to about 40 mm.

49. The fastener tab of claim 25, wherein the substantially inelastic region has a length of about 5 mm to about 25 mm.

50. The fastener tab of claim 25, wherein the substantially inelastic region has a length of about 10 mm.

51. The fastener tab of claim 25, wherein the substantially inelastic region comprises a laminate formed by one or more bonding methods chosen from the group consisting of: ultrasonic bonding, heat bonding and adhesive bonding.

52. The fastener tab of claim 25, wherein the fastener tab has non-parallel side edges.

* * * * *